United States Patent
Manalis et al.

[11] Patent Number: 6,156,216
[45] Date of Patent: Dec. 5, 2000

[54] METHOD FOR MAKING NITRIDE CANTILEVERS DEVICES

[75] Inventors: Scott R. Manalis, Santa Barbara, Calif.; Stephen C. Minne, Danville, Ill.; Calvin F. Quate, Stanford, Calif.

[73] Assignee: The Board of Trustees of the Leland Stanford Junior University, Palo Alto, Calif.

[21] Appl. No.: 09/152,746

[22] Filed: Sep. 14, 1998

Related U.S. Application Data

[63] Continuation-in-part of application No. 09/047,887, Mar. 25, 1998, Pat. No. 6,002,131.

[51] Int. Cl.[7] .................. B44C 1/22; C25F 3/00
[52] U.S. Cl. ...................................... 216/11; 216/2
[58] Field of Search ............................. 216/2, 11

[56] References Cited

U.S. PATENT DOCUMENTS

| | | | |
|---|---|---|---|
| 5,354,985 | 10/1994 | Quate ........................................ | 250/234 |
| 5,399,232 | 3/1995 | Albrecht et al. ........................ | 156/633 |
| 5,540,958 | 7/1996 | Bothra et al. ............................ | 427/535 |
| 5,546,375 | 8/1996 | Shimada et al. ........................ | 369/126 |
| 5,581,083 | 12/1996 | Majumdar et al. ..................... | 250/306 |

OTHER PUBLICATIONS

Hafeman, D. et al., "Light–addressable Potentiometric sensor for biochemical systems", Science, vol. 240, pp. 1182–85, 1988.

*Primary Examiner*—Randy Gulakowski
*Assistant Examiner*—Shamim Ahmed
*Attorney, Agent, or Firm*—Lumen Intellectual Property Services

[57] ABSTRACT

A method for making a silicon stylus protruding through a nitride layer is used to fabricate nitride micro-apertures, silicon styluses supported by nitride cantilever arms and charge sensitive silicon styluses supported by nitride cantilever arms. The method uses an anisotropic dry etch to define the apertures of the nitride micro-apertures and the apexes of the silicon styluses. Nitride apertures made by this method are useful for supporting micro-electronics and micro-optical devices. Surface probing devices with silicon styluses supported by nitride cantilever arms have applications in AFM and STM and are particularly useful in applications that require an electrical connection between the silicon stylus and external circuitry through the cantilever arm.

20 Claims, 7 Drawing Sheets

METHOD FOR MAKING NITRIDE CANTILEVERS DEVICES

RELATED APPLICATIONS

This application is a continuation-in-part of a patent application Ser. No. 09/047,887 filed Mar. 25, 1998, shown U.S. Pat. No. 6,002,131 which is herein incorporated by reference.

GOVERNMENT INTEREST

This invention was developed with government support under a grant from ONR JSEP contract no. N00014-91-J-1050. The government has certain rights in the invention.

FIELD OF THE INVENTION

This invention relates generally to methods of fabrication for surface probing devices. In particular this invention relates to the fabrication of nitride cantilever apertures for micro-electronics and micro-optical devices and the fabrication of silicon styluses supported by nitride cantilevers for surface analyses.

BACKGROUND

Surface analysis methods have advanced to achieve atomic resolution using a probing tip having an apex of atomic dimensions on surface probing devices. The probing tip is usually a tapered silicon structure, referred to as a stylus, with a base attached to a cantilever arm and a sharp apex that interacts with the surface being probed. The parts of a surface probing device include a stylus or aperture, a cantilever arm and a mounting section. In addition, a surface probing device may have an electrical connection from the stylus, through the cantilever arm, connected to external circuitry or may also have a reflective coating on the cantilever arm. The electrical connection and the reflective coating provide different ways to measure the response of the stylus apex to the surface being analyzed.

An apparatus that uses a surface probing device for surface analysis involves a scanning process. During the scanning process the stylus apex will respond to a surface characteristic. The response is monitored and generally held constant through a feed-back system that causes a slight change in the cantilever arm position. Two notable examples where these general principles apply are scanning tunneling microscopy (STM) and atomic force microscopy (AFM).

In STM a stylus apex of atomic dimensions on a cantilever arm follows the contour of a sample surface. Electrons tunnel through a near-field vacuum between the conductive apex of the stylus and a conducting sample creating a tunneling current. The tunneling current is very sensitive to changes in the distance between the stylus apex and the conductive sample surface. A feedback system is used to monitor and control the tunneling current at a constant value, and optical detection techniques such as interferometry or laser beam deflection are used to measure the resultant cantilever arm deflection during scanning.

AFM uses a stylus that is mounted on a cantilever arm that has a small spring constant and scans a surface such that repulsive inter-atomic forces between the surface and the stylus apex cause deflections in the cantilever arm position. Again, a feedback system is used to monitor and control the forces between the tip and sample, and an optical detection technique such as interferometry or laser beam deflection are used to measure the resultant cantilever arm deflection during the scanning process.

A new apparatus that uses a silicon stylus mounted on a cantilever arm is a scanning probe potentiometer (SPP). The SPP apparatus adapts the principles of light-addressable potentiometric sensor (LAPS) and combines them with a micro-scanning structure similar to that used in AFM and STM. The LAPS apparatus was developed to potentiometrically measure changes in pH, redox potential and transmembrane potential in a highly sensitive manner (see Hafeman et al., Science, Vol. 240, 1182 (1988)). The LAPS consists of an insulated semiconductor device which is immersed in an electrolyte. The sample of interest is placed on the surface of the insulator (at the insulator-electrolyte interface) and a bias voltage is generated such that the solution is negative with respect to the semiconductor. The insulator consists of a pH-sensitive material, such as silicon nitride or silicon oxinitride, or other charge-sensitive material. Electron-hole pairs are created in the semiconductor by a pulsed intensity-modulated light source, resulting in separation of charges in an area called the depletion region of the semiconductor. The electrons in the depletion region migrate, thereby causing a current of a magnitude that depends on the bias voltage and the chemistry of the sample at the adjacent insulator-solution interface. This movement of electrons yields a detectable alternating current in the external circuit. The adaptation of stylus apex surface probing device to LAPS provided a method for mapping charge distributions accurately for small surfaces.

Another application that uses a stylus supported by a cantilever arm construction is near field optical scanning microscopy (NSOM). Quate et al. describes NSOM in U.S. Pat. No. 5,354,985. In this technique the stylus and cantilever arm are a wave guide, whereby light escapes through a small hole or aperture in the apex of the stylus and is directed towards the sample. The cantilever arm is vibrated and variations in the resonant frequency are detected.

Several methods for fabricating surface probing devices with a stylus and cantilever arm have been reported. Bothra et al., U.S. Pat. No. 5,540,958, describe a method for making a stylus on a cantilever arm by first etching a silicon wafer with a mask to produce protruding shapes of a predetermined size and then depositing a second layer such as silicon oxide, by electron cyclotron resonance. Shimada et al., U.S. Pat. No. 5,546,375 describe making a stylus by forming a recessed cavity in a silicon wafer. The cavity is then used to define the structure of the stylus. In U.S. Pat. No. 5,399,232, Albrecht et al. describe a method of fabricating a cantilever arm and stylus again by forming a depressed area in a silicon wafer and using the depressed area to define stylus shape. In U.S. Pat. No. 5,581,083, Majumdar et al. describe a method for producing a hole at the apex of a stylus. The method uses an applied voltage to a metal coated tip causing evaporation of a metal coating and exposing the underlying silicon apex.

The combination of a stylus and cantilever arm is important for many modern surface probing methods. Each method of analysis requires a stylus and cantilever arm with properties tailored to the application at hand. Prior art teaches methods to fabricate silicon styluses on cantilever arms where the cantilever arms are made from silicon. One difficulty that can arise in fabricating surface probing devices with silicon cantilever arms is that the thickness of silicon is difficult to control by an etching processes. Additionally, it is beneficial for applications such as SPP to make surface probing devices that contain an electrically isolated silicon stylus that is connected to external circuitry through a conductive metal deposited on the nitride cantilever arm. Therefore, it is important to have methods for fabricating styluses and cantilever arms for surface probing devices, whereby the thicknesses of the cantilever arms are easy to control during the fabrication process and the cantilever contains an electrically isolated silicon tip.

OBJECTS AND ADVANTAGES

Accordingly, it is an object of the present invention to provide a method for the fabrication of nitride cantilever arms that are nitride and are useful as aperture devices that support micro-optical and micro-electronics devices.

Another objective of the invention is to provide a method for making surface probing devices, whereby the silicon material is restricted to styluses and mounting sections of the device and the cantilever arms are nitride. An advantage of this method is that the nitride layer is formed by a deposition processes rather than by an etching processes allowing for better control of the cantilever arm thickness. This method allows for the fabrication of nitride cantilever arms with spring constants engineered for the application at hand. Additionally a cantilever with an electrically isolated silicon stylus is useful in application where small currents are measured.

A third object of the invention is to provide a method for the fabrication of charge sensitive styluses supported by nitride cantilever arms. A surface probing device with a charge sensitive stylus and nitride cantilever arm is used in a SSP apparatus to accurately map charge distributions of a surface.

SUMMARY

The objects and advantages are accomplished by etching the top working surface of a wafer to form a silicon stylus with a predetermined area. Here and throughout the descriptions, working surfaces refer to the surfaces of interest that a specified operation is being performed on, and top refers to the working surfaces of the wafer that are part of the silicon stylus to be formed or formed while bottom refers to working surfaces that are not part of the silicon stylus to be formed or formed. The wafer is a silicon wafer, a p-doped silicon wafer, an n-doped silicon wafer, a p-doped silicon-on-insulator wafer or a p-doped silicon-on-insulator wafer. A silicon stylus is formed on the top working surface of the wafer by etching. Once the stylus has been formed, the stylus or the tip of the stylus can be ion implanted to alter the chemical composition. A nitride layer is deposited over the silicon stylus and the top silicon working surface of the wafer. A protective resist is spin coated on the nitride layer but not the nitride covered silicon stylus. The nitride covered silicon stylus is anisotropically dry etched to expose a desired underlying portion of the silicon stylus apex. The anisotropy dry etch etches the walls of the nitride coated silicon stylus slower than the surface perpendicular to the etch allowing for a controlled etching process that sharply defines the size and shape of the exposed silicon stylus apex. The amount of nitride removed is determined by the time of the etching process and defines the size of the aperture. After the aperture size has been determined by the dry etch, the resist is removed from the top silicon working surface of the wafer. A portion of the bottom silicon working surface of the wafer, the silicon oxide layer and the silicon stylus are etched away by any suitable method that will not significantly etch the nitride layer and thus produces a nitride micro-aperture.

A silicon stylus supported on a nitride cantilever arm is made by a similar method to that used for making nitride apertures except that the silicon stylus is not etched away. Instead, the bottom working surface of the silicon-on-insulator wafer is etched to the silicon-oxide layer at the base of the silicon stylus. A reflective material is coated on the bottom working surfaces and base of the silicon stylus. The reflective material is used in the optical detection system to measure deflection of the cantilever arm during a scanning process. Surface probing devices with silicon stylus apexes supported in a nitride cantilever arms have application in AFM and STM but are particularly useful in applications that require an electrical connection between the silicon stylus and external circuitry through the cantilever arm.

A charge sensitive silicon stylus supported in a nitride cantilever arm is made by providing a wafer for a top and bottom silicon working surface. The wafer is a silicon, an n-doped silicon, a p-doped silicon and silicon-on-insulator wafers. The top silicon working surface of the wafer is dry etched to form a silicon stylus with a predetermined area. A nitride layer is deposited on the silicon stylus and the top working surface of the wafer. The nitride covered working surface is spin coated with a resist leaving the nitride covered silicon stylus uncovered by the resist. The nitride covered silicon stylus is anisotropically etched to expose the silicon stylus apex. The resist is removed and a thin oxide layer is deposited over the exposed silicon stylus apex. A second layer of nitride is then deposited over the oxide layer on the silicon stylus apex. A portion of the bottom silicon working surface is etched away to producing a nitride cantilever arm with a charge sensitive stylus. A conductive path is establish from the charge sensitive silicon stylus through the nitride cantilever arm by any method that is suitable for the application at hand.

DETAILED DESCRIPTION

Figure 1A:
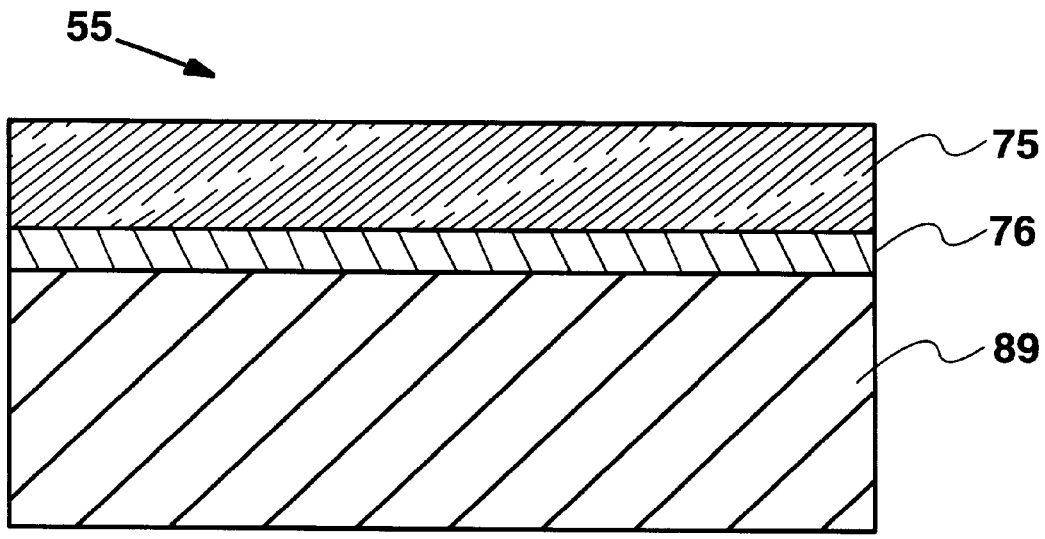
FIGS. 1A–D show the fundamental steps for making a nitride layer with a protruding silicon stylus.

FIGS. 1A–D show elementary steps for making a nitride layer with a protruding silicon stylus. A wafer 55 is provided for a top silicon working and a bottom silicon working surface. The wafer 55 is a silicon wafer or a silicon-on-insulator wafer. In the case shown, the wafer is a silicon-on-insulator wafer, with layer 75 that is p-doped, n-doped or un-doped silicon and layer 89 that is silicon. The layer 76 is a silicon oxide layer that is 0.1 to 5.0 $\mu$m (microns) thick sandwiched between the layers 75 and 89 (see FIG. 1A). The top working surface is etched to produce a silicon stylus 94 with an area ranging from 1 nm$^2$ (nanometers) to 1000 $\mu$m$^2$. The silicon stylus is a tapered silicon structure that has an apex and a base 96. The silicon stylus 94 can be doped at any time during the method described when the silicon stylus or stylus tip is exposed. The preferred method for doping the stylus is by ion implantation.

Figure 1B:
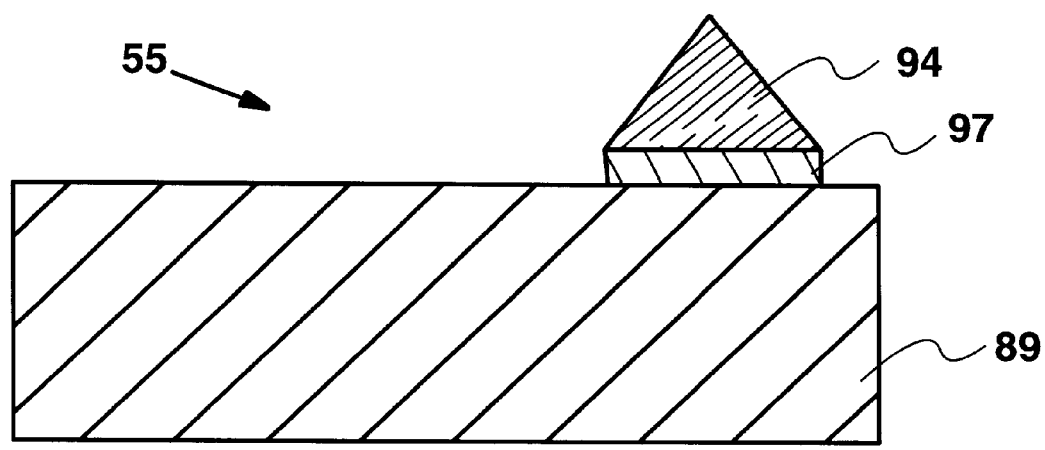
Figure 1C:
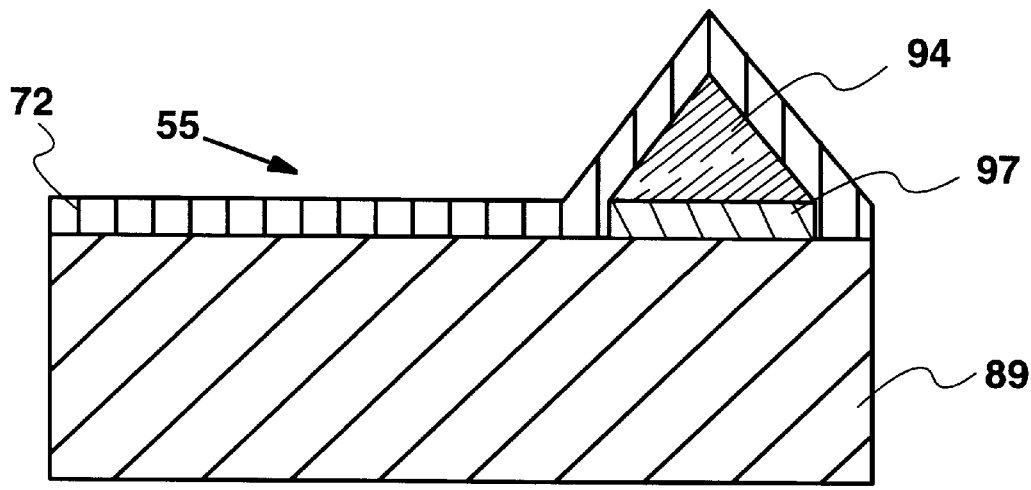
Figure 1D:
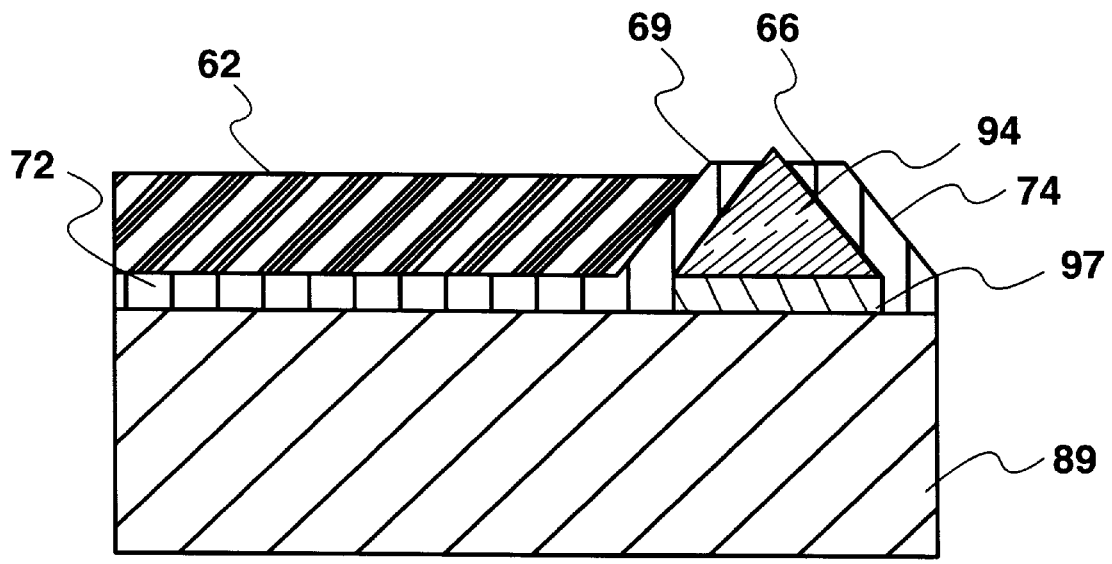

The silicon oxide 76 is etched away at the same time the silicon stylus is formed leaving a layer of silicon oxide 97 under the base 96 of the silicon stylus 94 (see FIG. 1B). A nitride layer 72 is deposited over the silicon stylus 94 and the top working surface of the wafer 55 (see FIG. 1C). The nitride layer 72 is deposited by chemical vapor deposition, low pressure chemical vapor deposition, plasma enhanced chemical vapor deposition, chemical deposition, evaporation and sputtering and is preferably 10 nm to 1.0 µm thick.

A protective resist 62 is spin coated on the nitride layer 72 so that the resist thickness is less than the height of the nitride covered silicon stylus 74. The nitride covered silicon stylus 74 is anisotropically dry etched to expose the underlying silicon stylus apex. The anisotropy dry etch etches the tapered walls 69 of the nitride covered silicon stylus 74 slower than the surface perpendicular to the etch allowing for a controlled etching process that sharply defines the stylus apex (see FIG. 1D). The silicon stylus 94 and silicon stylus tip 92 can be doped at any point in the method that the surface of silicon stylus 94 and silicon tip 92 are exposed. Doping of the silicon stylus 94 or silicon tip 92 is preferably accomplished by ion implanting.

The steps represented in FIGS. 1A–1D are common steps for making a nitride micro-aperture, a silicon stylus supported on a nitride cantilever arm and a charge sensitive silicon stylus supported on a nitride cantilever arm. Therefore, these steps will be referred to as the elementary steps for making a nitride layer with a protruding silicon stylus with further descriptions given to the additions or modifications to these steps.

Figure 2A:
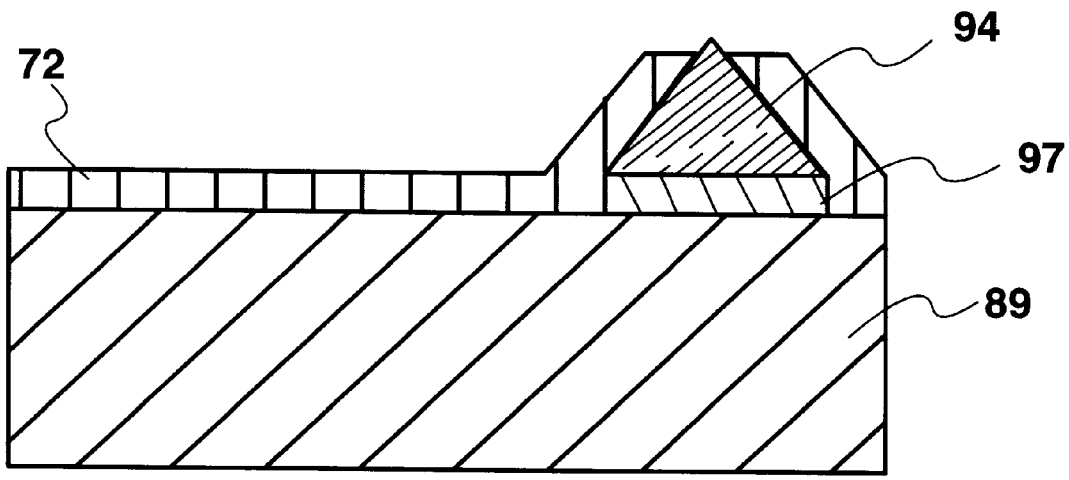
FIGS. 2A–B show the additional steps for making a nitride microaperture.
Figure 2B:
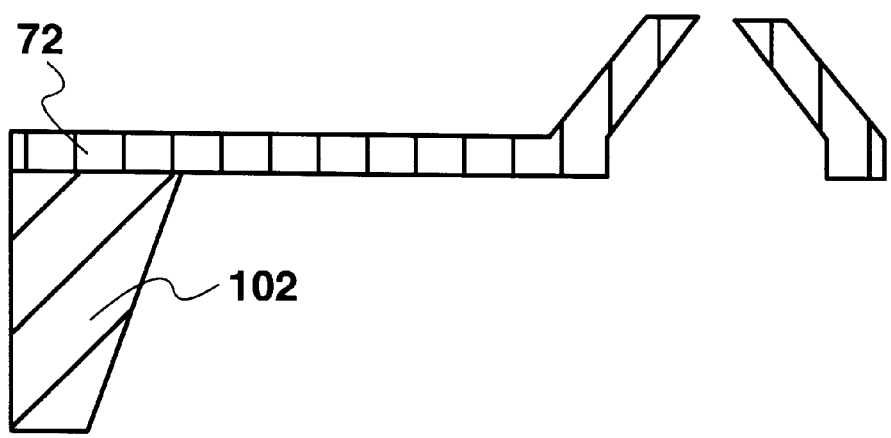

FIGS. 2A–2B illustrate the steps for making a nitride micro-aperture 63 in addition to the elementary steps (FIGS. 1A–1D) for making a nitride layer with a protruding silicon stylus. The aperture size is determined by dry etching the nitride covered silicon stylus 74 (see FIG. 1D) to expose a desired portion of the underlying silicon stylus apex 52. The resist 62 is removed from the top working surface of the wafer (see FIG. 2A). A portion of the silicon layer 89, all of the silicon oxide layer 97 and the silicon protruding tip 94 are etched away to make a nitride micro-aperture (see FIG. 2B). A portion of the silicon layer 89 is protected with a mask to leave a section of silicon 102 for mounting nitride micro-aperture.

FIGS. 3A–3D illustrate the steps for making a silicon stylus supported on a nitride cantilever arm, in addition to the elementary steps (FIGS. 1A–1D) for making a nitride layer with a protruding silicon stylus. The method differs from making a nitride micro-aperture in that the silicon stylus 94 is not etched away. The bottom working surface of the silicon-on-insulator wafer is etched to the silicon-oxide layer 97 at the base of the silicon stylus.

Figure 3A:
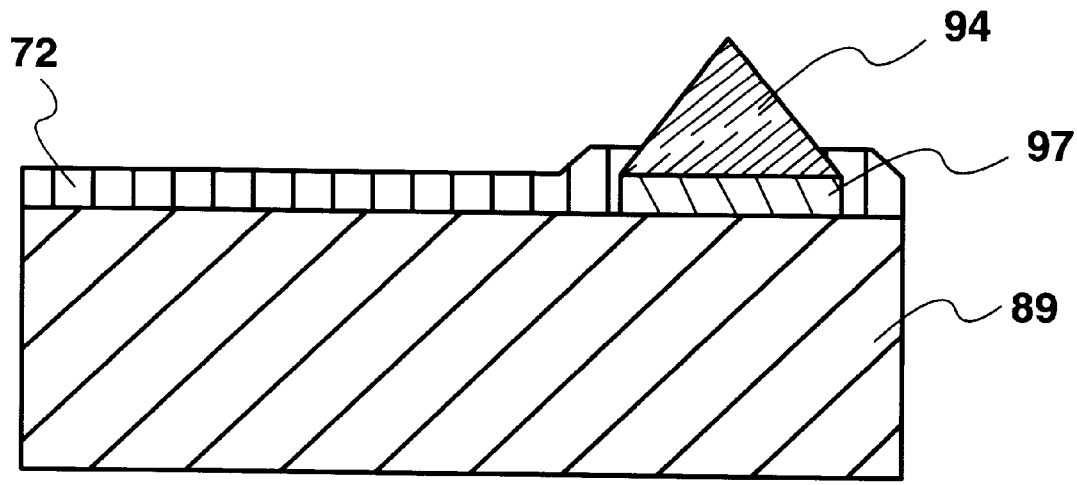
FIGS. 3A–D show the additional steps for making a silicon stylus supported by a nitride cantilever arm.
Figure 3B:
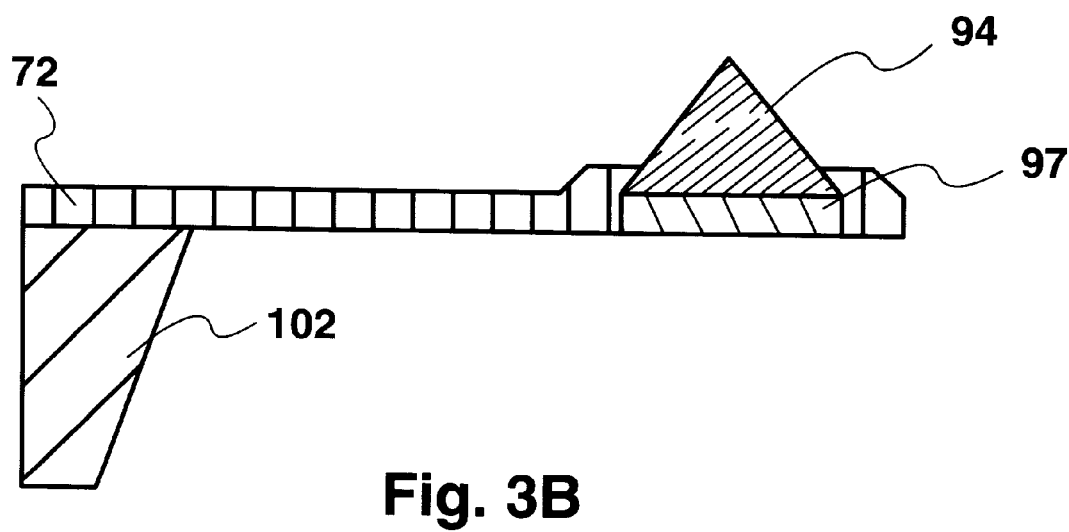
Figure 3C:
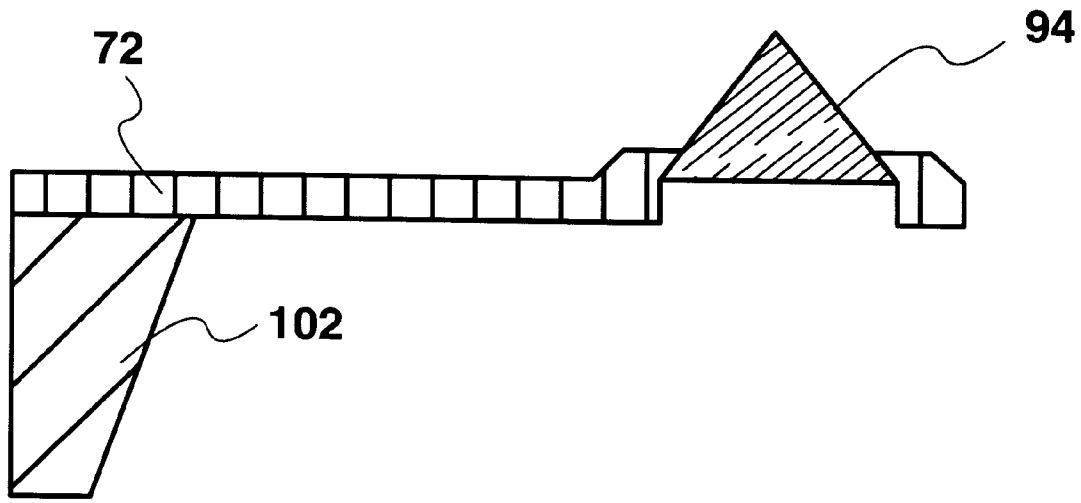
Figure 3D:
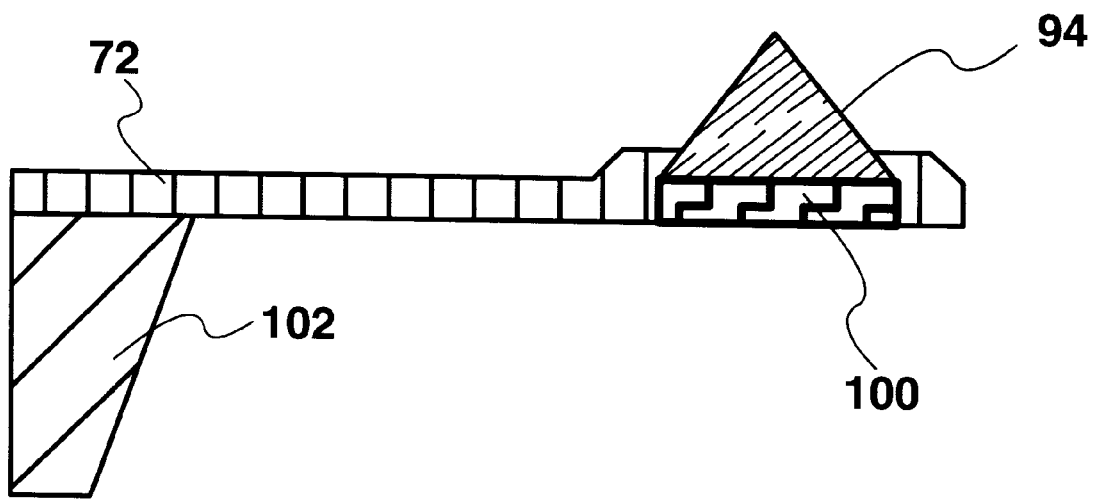

After the size of the exposed silicon stylus apex has been determined by the etching the nitride covered silicon stylus 74 (see FIG. 1D), the resist 62 is removed (FIG. 3A). The bottom working surface of the wafer is etched to the oxide layer 97 at the basil portion of the silicon protruding tip (FIG. 3B). A section of the silicon layer 89 is not etched away to leave a section 102 of silicon for mounting the cantilever. The oxide layer 97 at the base of the silicon protruding tip is 0.1 µm to 5.0 µm thick and can be removed (see FIG. 3C) remain as part of the structure. Whether or not the silicon oxide layer 97 is removed from the base of the protruding tip, a reflective material 100 is coated by electroplating, electrolysis or vapor deposition on the bottom working surface of the cantilever arm and base of the silicon stylus (see FIG. 3D). The reflective material 100 is any reflective material that can be deposited. The reflective material is used to measure deflection of a the cantilever arm using an optical detection technique well known in the art.

Figure 4A:
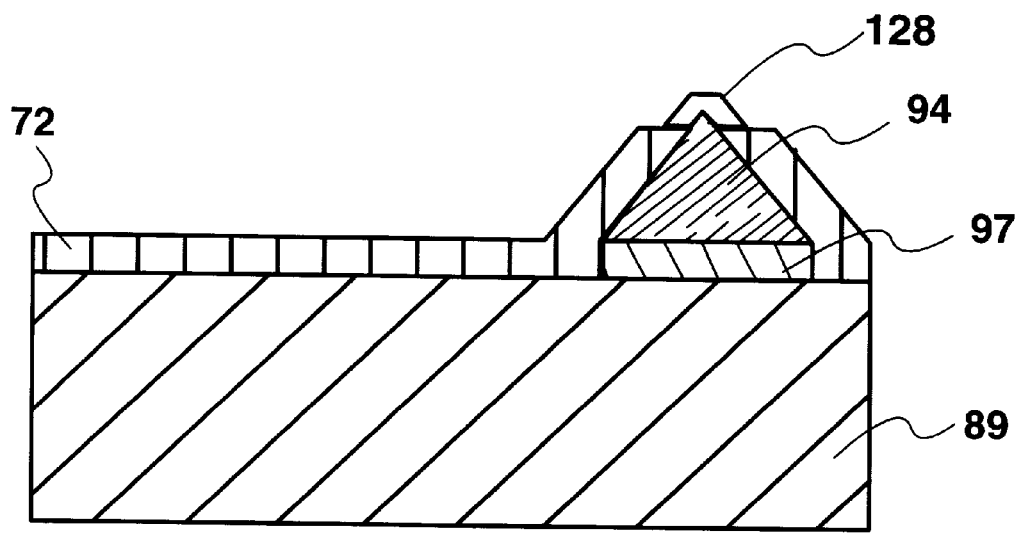
FIGS. 4A–C show the additional steps for making a charge sensitive silicon stylus supported by a nitride cantilever arm.
Figure 4B:
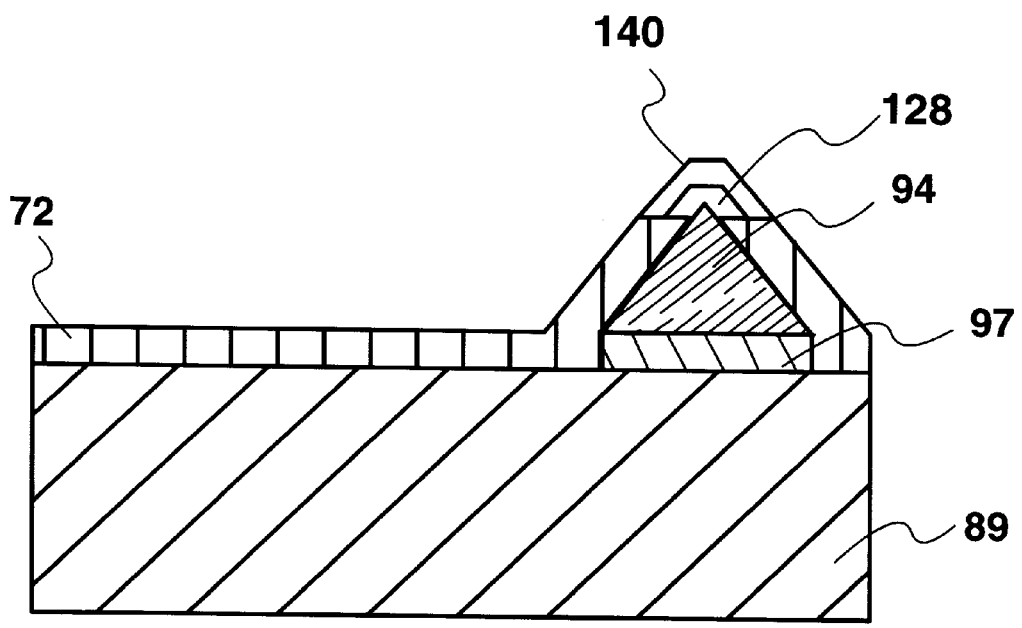
Figure 4C:
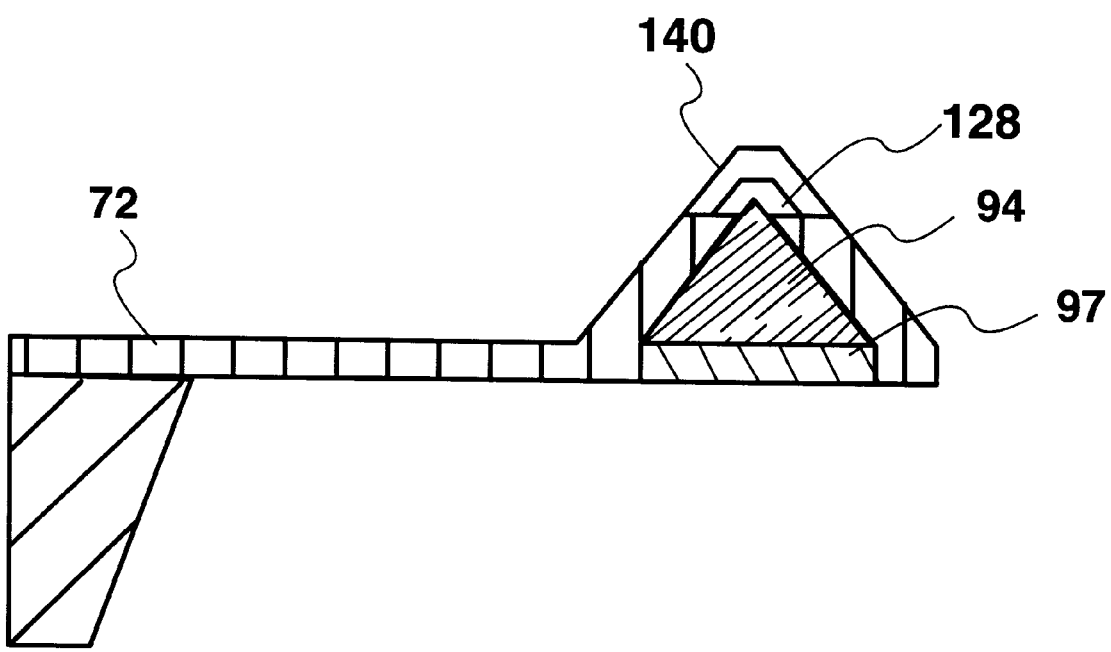

FIGS. 4A–4C illustrate the steps for making a charge sensitive silicon stylus supported on a nitride cantilever, in addition to the elementary steps (FIGS. 1A–1D) for making a nitride layer with a protruding silicon stylus. After the size of the exposed silicon stylus apex has been determined by dry etching the nitride covered silicon stylus 74 (see FIG. 1D) the resist 62 is removed and an oxide layer 128 is deposited over the exposed silicon stylus apex (FIG. 4A). The oxide layer 128 is preferably 0.01 µm to 10 µm thick and is deposited by plasma enhanced chemical vapor deposition, low temperature thermal deposition, evaporation, sputtering and spin on glass. Referring to FIG. 4B, a second layer of nitride 140 is deposited over the oxide layer 128 on the exposed silicon stylus apex. The second nitride layer is 0.01 to 2000 thick microns and deposited by chemical vapor deposition, low pressure chemical vapor deposition, plasma enhanced chemical vapor deposition, chemical deposition, evaporation and sputtering. Referring now to FIG. 4C, the silicon layer 89 is etched from the bottom working surface of the wafer leaving a portion of the silicon layer 120 for mounting cantilever arm. A conductive path can be establish form the charge sensitive silicon stylus through the nitride cantilever arm by any method that is suitable for the application at hand.

It will be clear to one skilled in the art that the above embodiment may be altered in many ways without departing from the scope of the invention. For example the base of the silicon stylus can partially etched to make a hollow silicon stylus. Accordingly, the scope of the invention should be determined by the following claims and their legal equivalents.

What is claimed:

1. A method of making a nitride layer with a protruding silicon stylus comprising the following steps:
    (a) providing a wafer for a top silicon working surface and a bottom silicon working surface, said wafer selected from the group consisting of a silicon wafer and a silicon-on-insulator wafer;
    (b) etching said top silicon working surface to make said silicon stylus of a predetermined area with a base and an apex;
    (c) depositing said nitride layer of a predetermined thickness on said top silicon working surface and said silicon stylus to produce a nitride covered working surface and a nitride covered silicon stylus;
    (d) spin coating said nitride covered working surface with a resist;
    (e) etching a predetermined area of said nitride covered silicon stylus to expose apex of said silicon stylus;
thereby, making a nitride layer with said protruding silicon stylus.

2. The method of claim 1 wherein said silicon stylus is a doped silicon stylus.

3. The method of claim 2 wherein said doped silicon stylus is doped by ion implantation.

4. The method of claim 1 wherein said silicon wafer comprises n-doped silicon and p-doped silicon.

5. The method of claim 1 wherein said predetermined area of said silicon stylus is 1 nm$^2$ to 1000 µm$^2$.

6. The method of claim 1 wherein said nitride layer is deposited by a method selected from the group consisting of chemical vapor deposition, low pressure chemical vapor deposition, plasma enhanced chemical vapor deposition, chemical deposition, evaporation and sputtering.

7. The method of claim 1 wherein said nitride layer is 10 nm to 1.0 µm thick.

8. The method of claim 1 wherein said predetermined area of said exposed silicon stylus apex is 1 nm$^2$ to 1000 µm$^2$.

9. The method of claim 1 wherein said nitride covered silicon stylus is anisotropically dry etched.

10. The method of claim 1 for making a nitride micro-aperture, comprising the following additional steps:
   (a) removing said resist from said nitride covered working surface;
   (b) etching away said bottom silicon working surface of said wafer and said silicon stylus to expose said nitride layer;
thereby, making said nitride micro aperture.

11. The method of claim 10 wherein said nitride micro-aperture supports a micro electronic device.

12. The method of claim 10 wherein said nitride micro-aperture supports an optical device.

13. The method of claim 1 to make a silicon stylus supported in a nitride cantilever arm, comprising the following additional steps:
   (a) removing said resist from said nitride layer;
   (b) etching said bottom silicon working surface of said wafer to expose said nitride layer and said base of said silicon stylus;
thereby making said silicon stylus supported by a nitride cantilever.

14. The method of claim 13 wherein a reflective coating is deposited on said base of said silicon stylus.

15. The method of claim 13 wherein said reflective coating is selected from the group consisting of electroplating, electrolysis and vapor deposition.

16. The method of claim 1 to make a nitride cantilever arm with a charge sensitive stylus apex, comprising the following additional steps:
   (a) removing said resist from said nitride covered working surface;
   (b) depositing an oxide layer of a predetermined thickness on said exposed apex of said silicon stylus;
   (c) depositing a second nitride layer of a predetermined thickness on said oxide layer;
   (d) etching said bottom silicon working surface to expose said nitride layer and said base of said silicon stylus;
thereby, producing said nitride cantilever arm with a charge sensitive stylus.

17. The method of claim 16 wherein said second nitride layer is deposited by a method from a group consisting of chemical vapor deposition, low pressure chemical vapor deposition, plasma enhanced chemical vapor deposition, chemical deposition, evaporation and sputtering.

18. The method of claim 16 wherein said second nitride layer is 200 Angstroms to 2000 Angstroms thick.

19. The method of claim 16 wherein said oxide layer is deposited by a method selected from the group consisting of plasma enhanced chemical vapor deposition, low temperature thermal deposition, evaporation, sputtering and spin on glass.

20. The method of claim 16 wherein said oxide layer is 0.01 $\mu$m to 10.0 $\mu$m thick.

* * * * *